(12) United States Patent
Klyamkin et al.

(10) Patent No.: US 8,088,284 B2
(45) Date of Patent: Jan. 3, 2012

(54) SYSTEM AND METHOD FOR MEASURING THE CONCENTRATION OF MAGNETIC BALLAST IN A MOVING SLURRY

(75) Inventors: Simone Klyamkin, Brighton, MA (US); Steven Woodard, Cumberland, ME (US)

(73) Assignee: Cambridge Water Technology, Inc., Cambridge, MA (US)

( * ) Notice: Subject to any disclaimer, the term of this patent is extended or adjusted under 35 U.S.C. 154(b) by 741 days.

(21) Appl. No.: 12/288,825

(22) Filed: Oct. 23, 2008

(65) Prior Publication Data

US 2010/0101309 A1     Apr. 29, 2010

(51) Int. Cl.
*B01D 35/06* (2006.01)
*G01R 33/12* (2006.01)
*G01N 33/00* (2006.01)
*G01B 7/00* (2006.01)

(52) U.S. Cl. ........ 210/695; 210/222; 210/223; 324/204; 324/239; 73/61.41

(58) Field of Classification Search ................. 73/61.41; 210/695, 222, 223; 324/204, 239
See application file for complete search history.

(56) References Cited

U.S. PATENT DOCUMENTS

| | | | |
|---|---|---|---|
| 6,824,692 B2 | 11/2004 | Binot et al. | |
| 7,557,566 B2 * | 7/2009 | Kordonski et al. | ........... 324/239 |

* cited by examiner

*Primary Examiner* — David A Reifsnyder
(74) *Attorney, Agent, or Firm* — Iandiorio Teska & Coleman (57) ABSTRACT

A system for measuring the concentration of magnetic ballast in a moving slurry including a detection conduit surrounded by a set of coaxial detection coils configured to receive the moving slurry, a reference conduit surrounded by a set of coaxial coils, an AC power source for establishing a magnetic field in one of the detection coils and one of the reference coils, and a measurement subsystem for measuring the differential induced voltage between one of the set of coaxial detection coils and one of the set of coaxial reference coils to determine the concentration of the magnetic ballast in the moving slurry.

33 Claims, 7 Drawing Sheets

SYSTEM AND METHOD FOR MEASURING THE CONCENTRATION OF MAGNETIC BALLAST IN A MOVING SLURRY

FIELD OF THE INVENTION

This invention relates to a system and method for measuring the concentration of magnetic ballast in a moving slurry.

BACKGROUND OF THE INVENTION

Some wastewater treatment systems and methods use magnetically separable particles, e.g., magnetite, as a settling aid. See e.g., U.S. Pat. No. 6,099,738 to Wechsler et al. entitled "Method and System For Removing Solutes From a Fluid Using Magnetically Conditioned Coagulation", and U.S. Publication No. 2008/0203015 entitled "System and Method For Enhancing An Activated Sludge Process", both by the inventive entity hereof and incorporated by reference herein. As disclosed therein, magnetically separable particles, or magnetic ballast, such as magnetite, become enmeshed into the chemical and/or biological flocs. The magnetic ballast adds mass to the flocs which significantly increases their effective specific gravity and causes them to settle at a much faster rate in the clarifier. The result is the clarifier(s) of these systems functions at much higher surface overflow rate (SOR) and typically occupies a footprint which may be 10 to 20 times smaller than the clarifier of conventional wastewater treatment systems which do not utilize magnetically separable particles.

Such wastewater treatment systems and methods often need to monitor the level of the magnetic ballast in the moving slurry of the various components of the system, e.g., the aeration tank(s), the mixing tank(s), the weighting agent impregnation subsystem, various areas of one or more clarifiers, e.g., the sludge blanket, various lines and pipes of the system, and the like.

Conventional methods for determining the concentration of magnetic ballast in moving slurry of such systems typically include manually extracting a sample from the desired location in the system. The sample is then sent to a laboratory where a time consuming and cumbersome process is performed to determine the concentration of magnetic ballast in the moving slurry. Other conventional systems use a static cell which is cumbersome and difficult to use.

Thus, there is a need for a system and method which can automatically and continuously measure the concentration magnetic ballast in the moving slurry of a wastewater treatment system.

BRIEF SUMMARY OF THE INVENTION

It is therefore an object of this invention to provide a system and method for measuring the concentration of magnetic ballast in a moving slurry.

It is a further object of this invention to provide such a system and method which can automatically and continuously measure the concentration magnetic ballast in the moving slurry.

It is a further object of this invention to provide such a system and method which reduces the time required to determine the concentration of magnetic ballast in a moving slurry.

It is a further object of this invention to provide such a system and method which is less complex.

It is a further object of this invention to provide such a system and method which is easy to use.

It is a further object of this invention to provide such a system and method which is reduces the cost to determine the concentration of magnetic ballast in a moving slurry.

The subject invention, however, in other embodiments, need not achieve all these objectives and the claims hereof should not be limited to structures or methods capable of achieving these objectives.

This invention features a system for measuring the concentration of magnetic ballast in a moving slurry including a detection conduit surrounded by a set of coaxial detection coils configured to receive the moving slurry, a reference conduit surrounded by a set of coaxial coils, an AC power source for establishing a magnetic field in one of the detection coils and one of the reference coils, and a measurement subsystem for measuring the differential induced voltage between one of the set of coaxial detection coils and one of the set of coaxial reference coils to determine the concentration of the magnetic ballast in the moving slurry.

In one embodiment, the measured voltage may be proportional to the concentration of the magnetic ballast in the moving slurry. One of the set of coaxial detection coils may be connected in series with one of the set of coaxial reference coils and with the AC power source and the other of set of coaxial detection coils may be connected back-to-back with the other of the set of coaxial reference coils and with the measurement subsystem. The system may include a DC coil coupled to a DC power source surrounding one of the detection coils and the detection conduit for establishing a magnetic field which stops and collects magnetic ballast in the detection conduit so that the measurement subsystem can measure very low concentrations of magnetic ballast in the moving slurry. The system may include a permanent magnet surrounding one of the detection coils and the detection conduit for establishing a magnetic field which stops and collects magnetic ballast in the detection conduit so that the measurement subsystem can measure very low concentrations of magnetic ballast in the moving slurry. The very low concentrations of magnetic ballast in the moving slurry may be less than about 0.01 g/L. The system may include a pumping subsystem for directing the moving slurry to the detection conduit. The pumping subsystem may direct the moving slurry from a component of a wastewater treatment system to the detection conduit and back to the component of the wastewater treatment system. The one or both of the detection conduit and/or the reference conduit may be immersed in the moving slurry of a component of a wastewater treatment system. The detection coil may be immersed in the moving slurry of a component of a wastewater treatment system and the reference conduit is disposed outside the component of the wastewater treatment system. The component of a wastewater treatment system may include a component chosen from the group consisting of: a reaction tank, a mixing tank, an aeration tank, a settling tank, a clarifier, one or more lines and/or pipes, an impregnation subsystem, a return activated sludge subsystem, a weighting agent, recovery subsystem, and a wasting subsystem. The moving slurry may include a mixed liquor defined by a concentration of mixed liquor suspended solids and biological flocs impregnated with magnetic ballast suspended in the mixed liquor. The moving slurry may include chemical flocs and/or suspended solids having magnetic ballast therein and/or suspended magnetic ballast. The moving slurry may include a sludge blanket in a clarifier. The measurement system may be configured to determine the location of the sludge blanket in the clarifier. The set of coaxial reference coils and each of the set of coaxial detection may be identical and symmetrical. The magnetic ballast may include magnetically separable particles. The magnetically separable particles may include magnetite.

This invention also features a method for measuring the concentration of magnetic ballast in a moving slurry, the method including providing a detection conduit surrounded by a set of coaxial detection coils configured to receive the moving slurry, providing a reference conduit surrounded by a set of coaxial reference coils, establishing a magnetic field in one of the detection coils and one of the reference coils, and measuring the differential induced voltage between one of the set of coaxial detection coils and one of the set of coaxial reference coils to determine the concentration of the magnetic ballast in the moving slurry.

In one embodiment, the measured voltage may be proportional to the concentration of the magnetic ballast in the moving slurry. The method may include the step of establishing a magnetic field which stops and collects magnetic ballast in the detection conduit so that the measurement subsystem can measure very low concentrations of magnetic ballast in the moving slurry. The very low concentrations of magnetic ballast in the moving slurry may be less than about 0.01 g/L. The method may include the step of directing the moving slurry to the detection conduit. The method may include the step of directing the moving slurry from a component of a wastewater treatment system to the detection conduit and back to the component of a wastewater treatment system. The method may include the step of immersing one or both of the detection conduit and/or the reference conduit in the moving slurry of a component of a wastewater treatment system. The method may include the step of immersing the detection conduit in the moving slurry and disposing the reference conduit outside the component of the wastewater treatment system. The component of a wastewater treatment system may include a component chosen from the group consisting of: a reaction tank, a mixing tank, an aeration tank, a settling tank, a clarifier, one or more lines and/or pipes, an impregnation subsystem, a return activated sludge subsystem, a weighting agent recovery subsystem, and a wasting subsystem. The moving slurry may include a mixed liquor defined by a concentration of mixed liquor suspended solids and biological flocs impregnated with magnetic ballast suspended in the mixed liquor. The moving slurry may include chemical flocs and/or suspended solids having magnetic ballast therein and/or suspended magnetic ballast. The moving slurry may include a sludge blanket in a clarifier. The method may include the step of determining the location of the sludge blanket in the clarifier. Each of the set of coaxial reference coils and each of the set of coaxial detection coils may be identical and symmetrical.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

As discussed in the Background section above, some wastewater treatment systems and methods, such as '738 patent and the '015 publication cited supra, need an easy, automatic, continuous, and inexpensive system and method to monitor the level of the magnetic ballast in the moving slurry of various components of the system.

Figure 1:
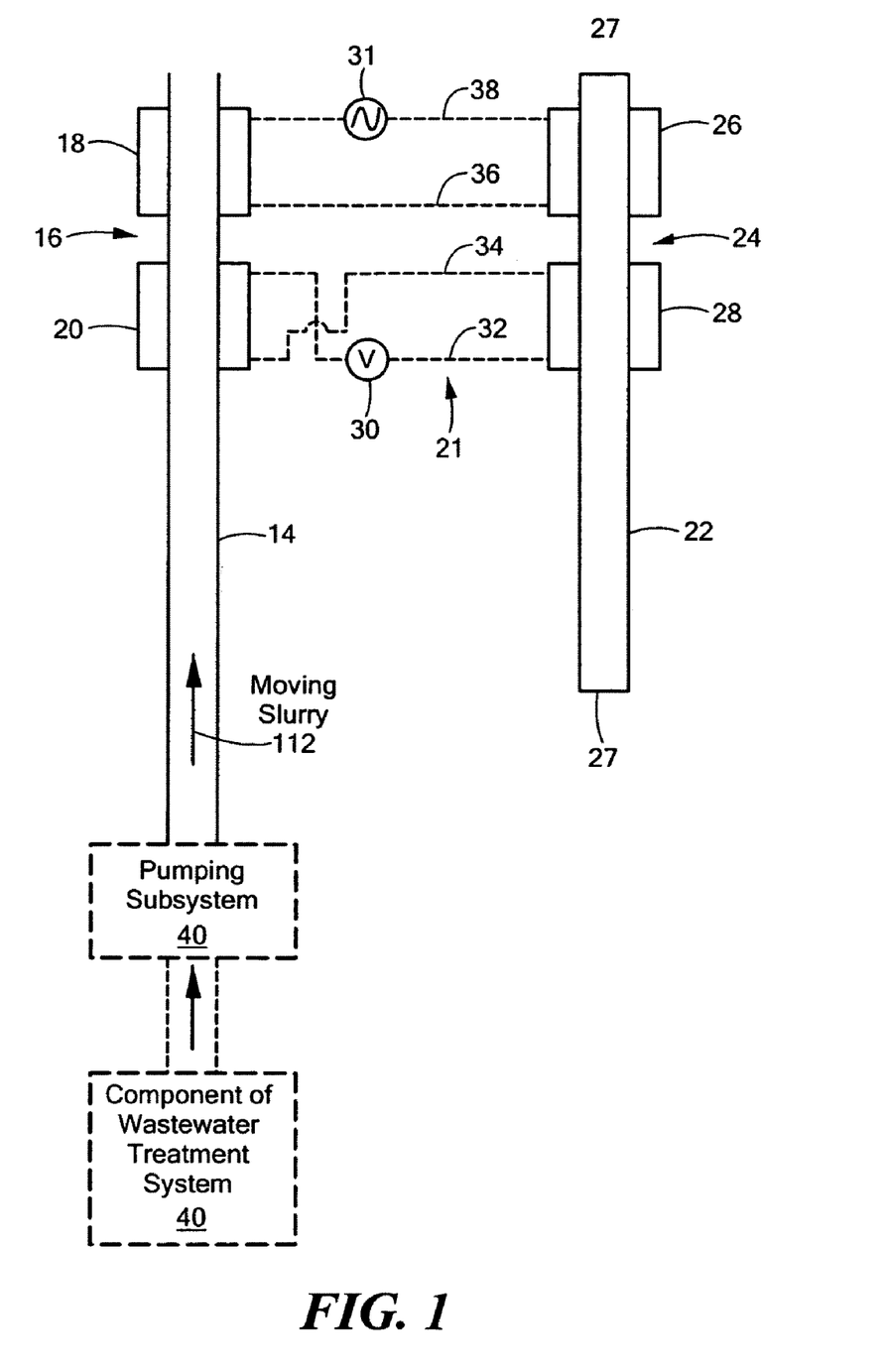
FIG. 1 is a schematic side-view of one embodiment of the system for measuring the concentration of magnetic ballast in a moving slurry of this invention.

System 10, FIG. 1, for measuring the concentration of magnetic ballast in moving slurry 12 of this invention provides a solution to such a need. System 10 includes detection conduit 14 which receives and is filled with moving slurry 12 having magnetic ballast therein. Detection conduit 14 is surrounded by set 16 of coaxial detection coil 18 and detection coil 20. System 10 also includes reference conduit 22, which is empty, e.g., is filled with ambient air and is surrounded by set 24 of reference coil 26 and reference coil 28. In one design, caps 27 and 29 may be secured on reference conduit 22 so that it may be submerged in moving slurry 12 (discussed below). AC power source 31 establishes a magnetic field in detection coil 20 and reference coil 28. Measurement subsystem 30, e.g., a voltmeter or similar type device, measures the differential voltage induced between detection coil 20 and reference coil 28 to determine the concentration of the magnetic ballast and moving slurry 12 in detection conduit 14. The voltage measured by measurement subsystem with circuit 21 comprised of detection coil 20 and reference coil 28 connected by leads 32 and 34 is proportional to the concentration of magnetic ballast in moving slurry 12 located inside detection conduit 14 when it contains moving slurry 12 with magnetic ballast therein and reference conduit 22 is empty.

In one embodiment, moving slurry 12 may include a mixed liquor defined by the concentration of the mixed liquor suspended solids and biological flocs impregnated with magnetic ballast suspended in the mixed liquor, See, e.g., U.S. Patent Publication No. 2008/0203015 cited above. Moving slurry 12 may also include chemical flocs or suspended solids having magnetic ballast and/or suspended magnetic ballast, or any combination thereof. See, e.g., U.S. Pat. No. 6,099,738 cited above.

In one example, detection coil 18 is connected in series with reference coil 26 to provide strict equality of the alternating currents in them. Preferably, detection coil 20 is connected back-to-back, or anti-phase, with reference coil 28. This provides meeting direction and subtraction of their inductive voltages by measurement subsystem 30. Such a configuration provides system 10 with the ability to measure the concentration of magnetic ballast in moving slurry 12 at concentrations in the range of about 0.1 g/L to about 10 g/L and higher. Preferably, detection coil 18, detection coil 20, reference coil 26, and reference coil 28 are identical and symmetrical The result is that system 10 automatically, continuously, and easily measures the concentration of magnetic ballast in moving slurry 12. Thus, system 10 eliminates the need to manually extract a sample of moving slurry and send it to the laboratory or to use a static sample cell to determine the concentration of magnetic ballast in moving slurry 12. Thus, system 10 saves time and money.

In one embodiment, system 10 includes pumping subsystem 40 for directing moving slurry 12 to detection conduit 14. Pumping subsystem 40 typically directs moving slurry 12 from component 42 of a wastewater treatment system, discussed in further detail below.

Figure 2:
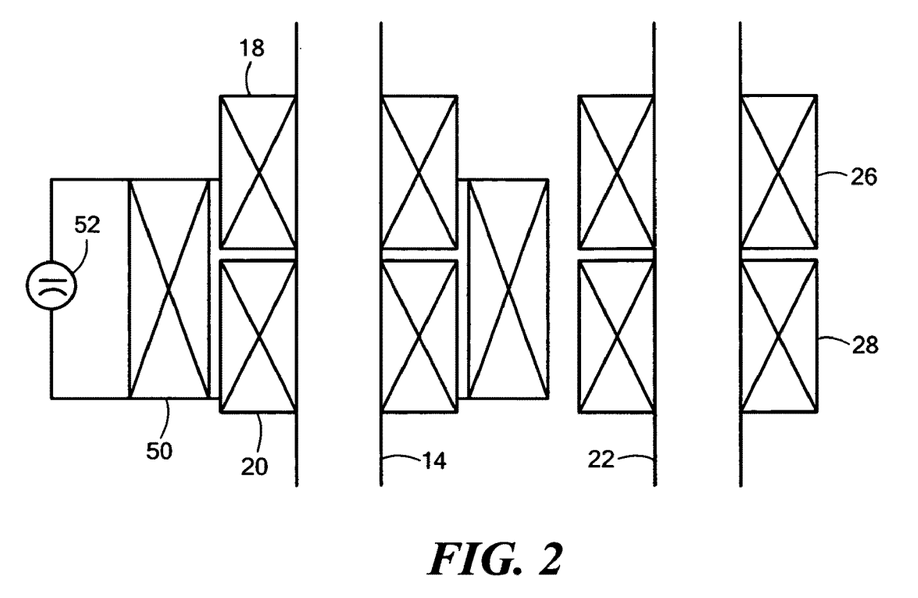
FIG. 2 is a schematic side view of the system shown in FIG. 1 including a DC coil about the detection conduit used for determining very low concentrations of magnetic ballast in the moving slurry.
Figure 3:
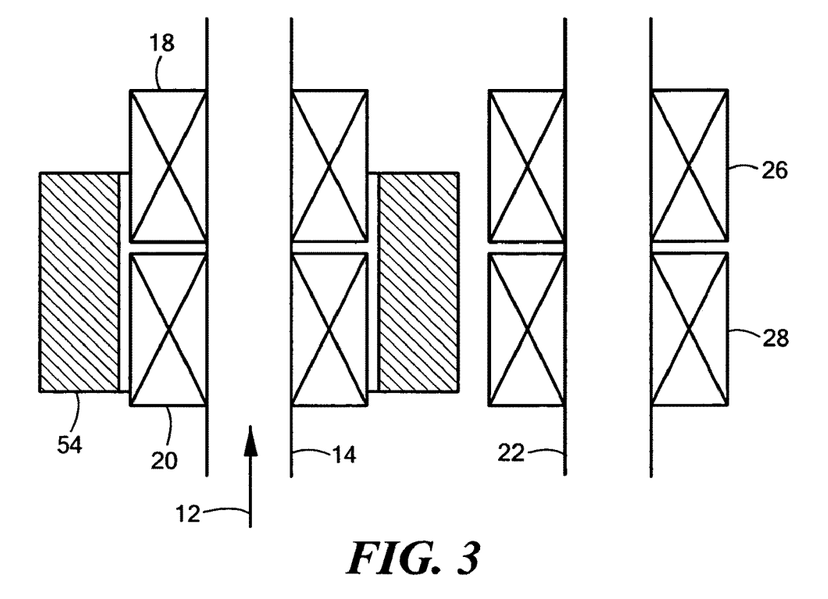
FIG. 3 is a schematic side view of the system shown in FIG. 1 including a permanent magnet about the detection conduit used for determining very low concentrations of magnetic ballast in the moving slurry.

System 10, FIG. 2, where like parts have been given like numbers, may include DC coil 50 which surrounds detection conduit 14 and detection coil 20. DC coil is typically coupled to DC power source 52. In other designs, system 10, FIG. 3, where like parts have been given like numbers, may include permanent magnet 54 which surround detection conduit 14 and detection coil 20. DC coil 50 with DC power source 52, FIG. 2, and/or permanent magnets 54, FIG. 3, are used for the detection of very low concentrations of magnetic ballast in moving slurry 12, e.g., less than about 0.01 g/L. The magnetic field applied by DC coil 50 and/or permanent magnets 54 to detection conduit 14 stops and collects the magnetic ballast in detection conduit 14. The amount of the stopped ballast in detection conduit 14 is measured by measurement subsystem 30, FIG. 1, and is proportional to the flow of moving slurry 12, collection time, and ballast concentration. Thus, the concentration of magnetic ballast of the collected magnetic ballast is calculated from the flow rate, collection time, and the final inductive voltage measured. After being measured, the collected ballast is typically flushed out by increased flow and/or by switching of DC coil 50 and/or by removing permanent magnets 54 for a short time.

Figure 4:
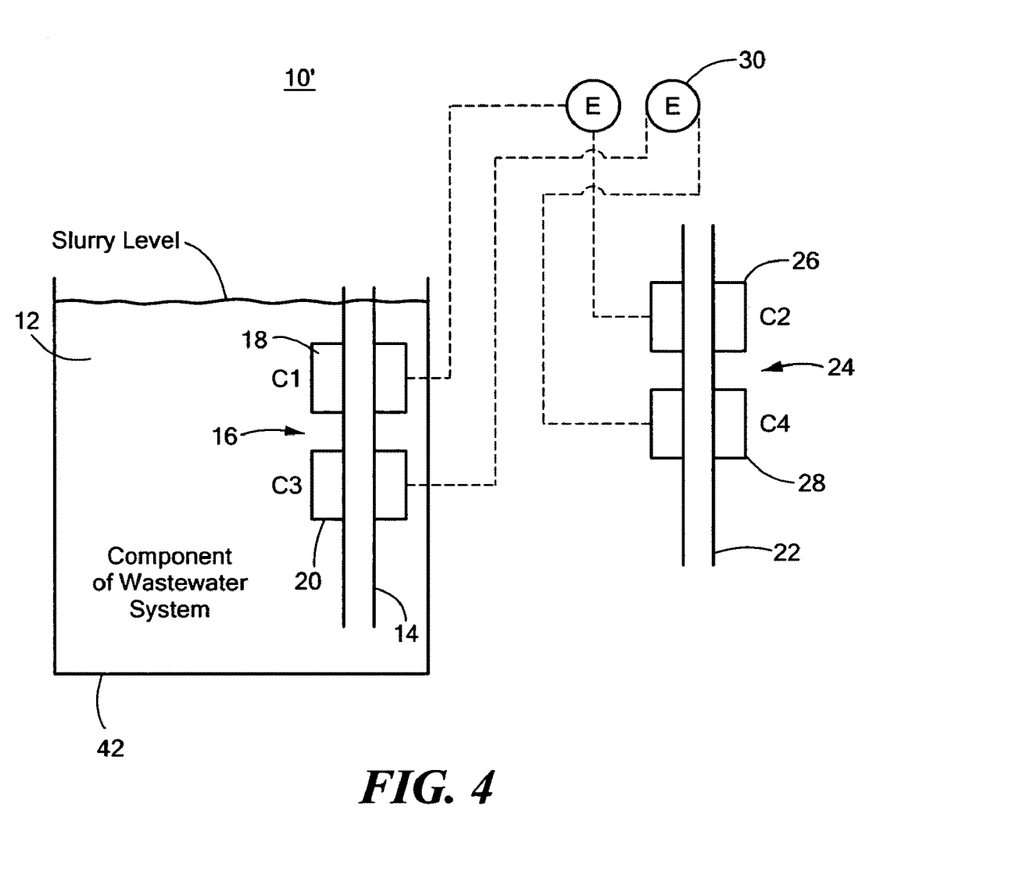
FIG. 4 is a schematic side-view of yet another embodiment of the system for measuring the concentration of magnetic ballast in a moving slurry of this invention.

In another design, system 10', FIG. 4, where like parts have been given like numbers, may be configured so that detection conduit 14 with set 16 of detection coils 18 and 20 is immersed in moving slurry 12 having magnetic ballast therein. For example, conduit 14 with set 16 of detection coils 18 and 20 may be immersed in the moving slurry which is located in a component 42 of a wastewater treatment system (discussed below). In this design, reference conduit 22 with set 24 of reference coils 26, 28 is empty and is disposed outside component 42 of the wastewater treatment system.

Figure 5:
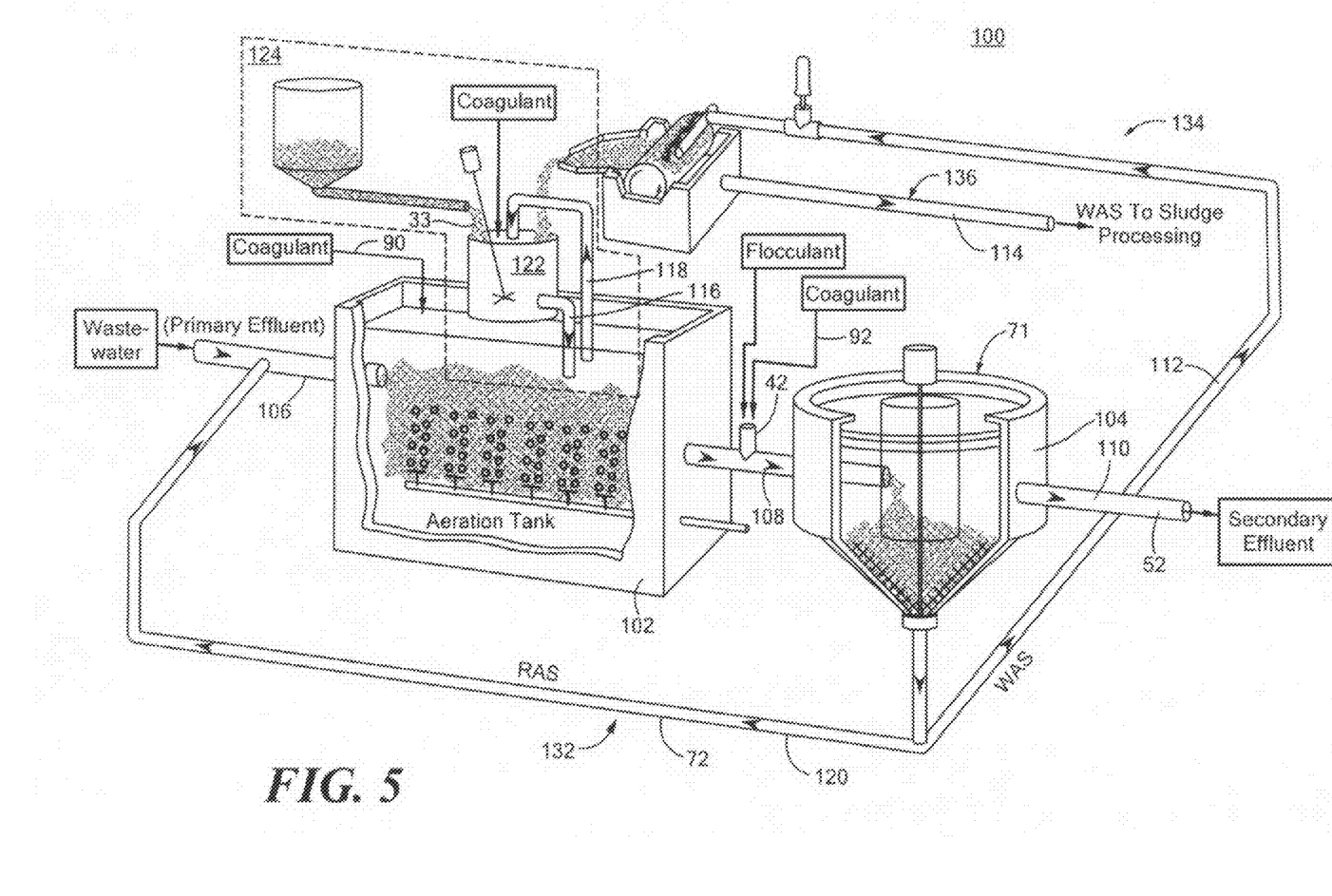
FIG. 5 is a three-dimensional view showing components of a typical wastewater treatment system which can utilize the system for measuring the concentration of magnetic ballast in a moving slurry of this invention.

In one example, component 42, FIGS. 1 and 4, may include any of the various components or subsystems of wastewater treatment systems, e.g., as disclosed in the '216 patent application, the '738 patent, cited supra, or any other wastewater treatment system known to those skilled in the art. For example component 40 may include any of the various components of wastewater treatment system 100, FIG. 5, e.g., aeration tank 102, clarifier 104, any of lines 106, 108, 110, 112, 114, 116, 118, or 120, tank 122 of weighting agent impregnation subsystem 124, return activated sludge subsystem 132, weighting agent recovery subsystem 134, and/or wasting subsystem 136. Further details regarding the operation of system 100 and the various components discussed above are disclosed in detail in the '015 publication cited supra.

Figure 6:
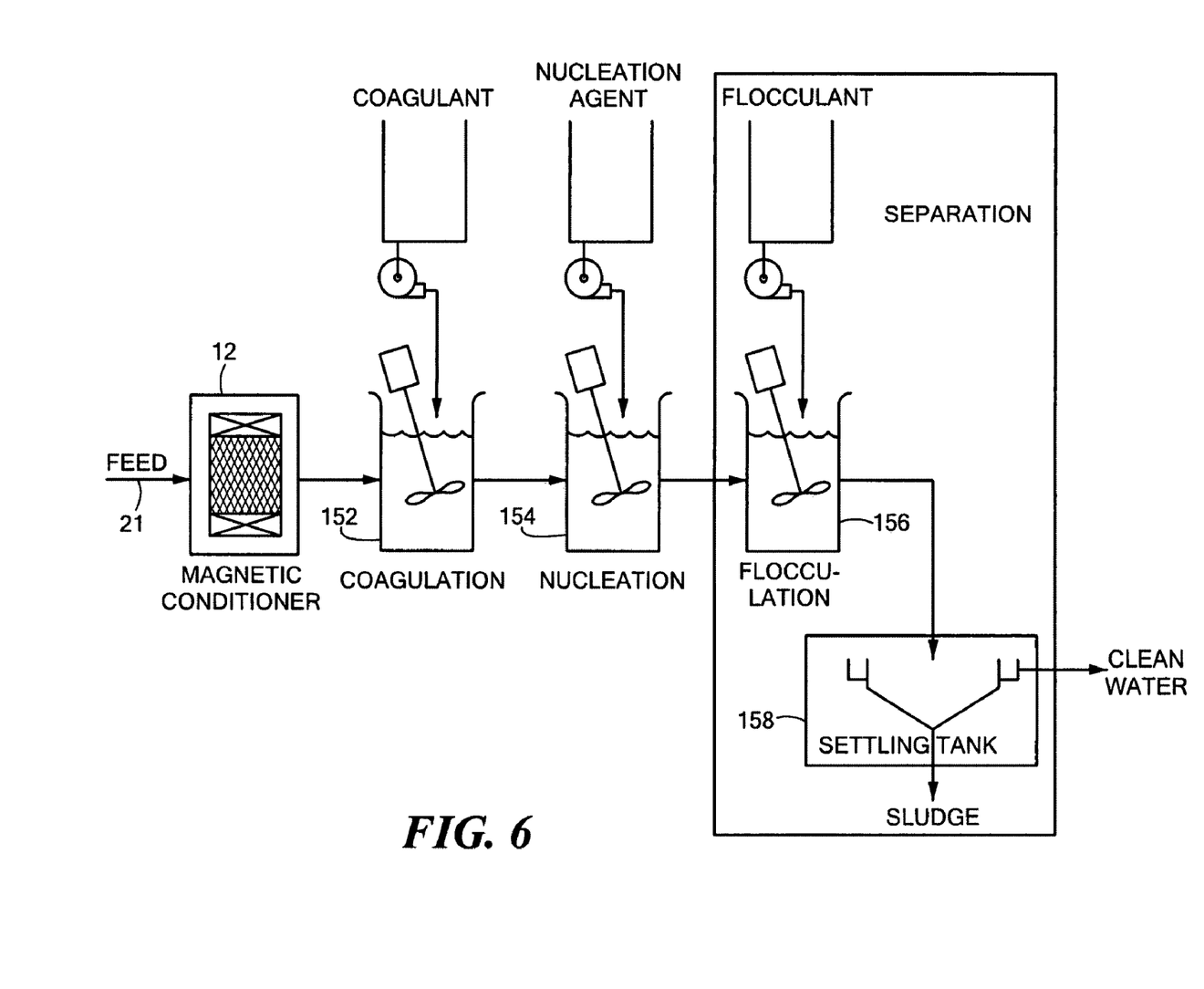
FIG. 6 is a schematic block diagram showing components of a another typical wastewater treatment system which can utilize the system for measuring the concentration of magnetic ballast in a moving slurry of this invention.

Component 40 of a wastewater treatment system may also include any of the various components from wastewater treatment system 150, FIG. 6, as disclosed in the '738 patent, e.g., a reaction tank, such as coagulation tank 152, nucleation tank 154 and/or flocculation tank 156. Components 40 may also include settling tank 158. Further details concerning the components and operation of wastewater treatment system 150 are disclosed in detail in the '738 Patent.

Figure 7:
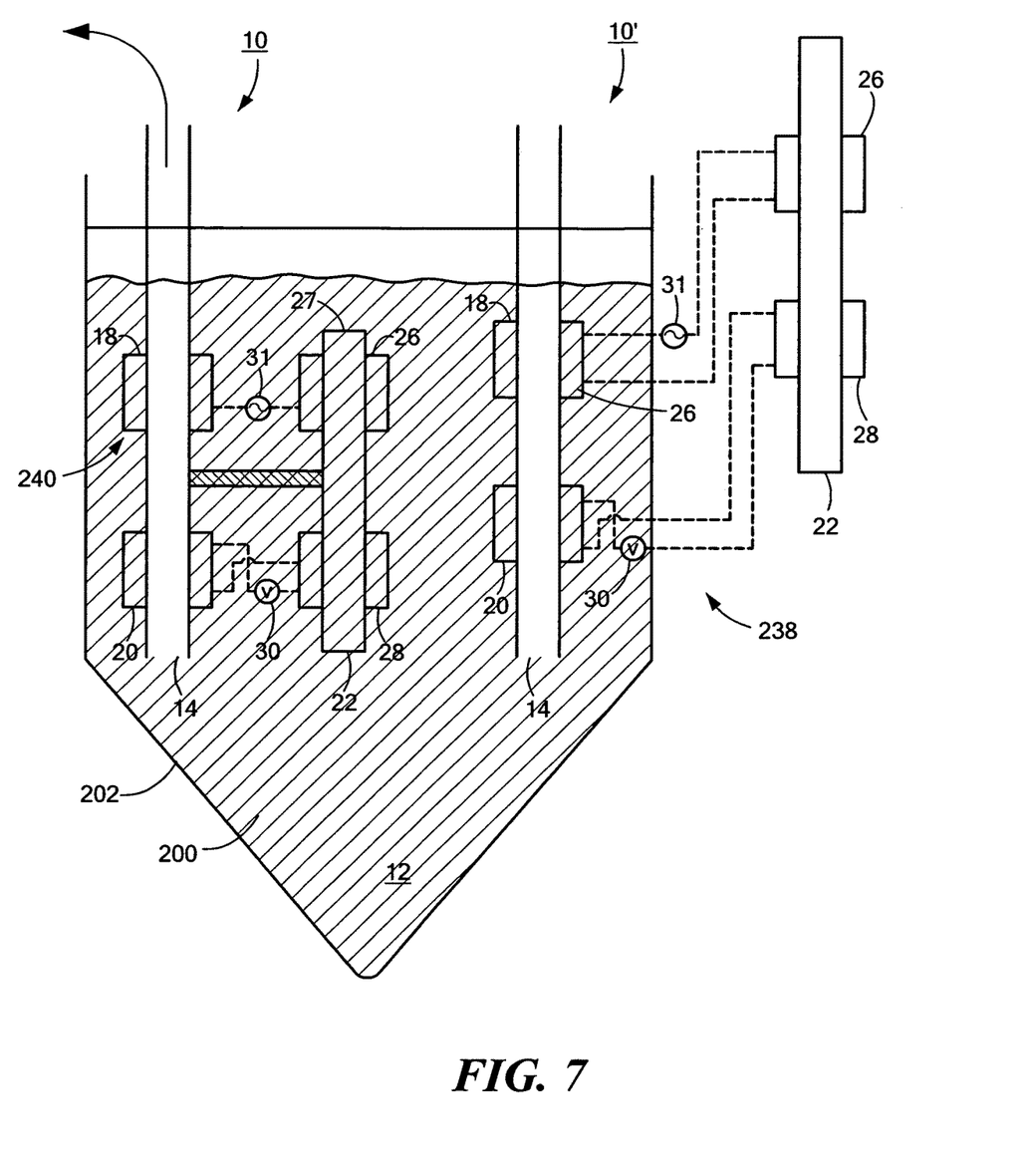
FIG. 7 is a schematic side-view showing examples of system shown in FIGS. 1 and 4 used to measure the concentration of magnetic ballast in a sludge blanket of a clarifier.

In one embodiment, system 10', FIG. 7, where like parts have been given like numbers, may be used to measure the concentration of magnetic ballast in sludge blanket 200 located in clarifier 202. In one example, system 10', indicated at 238, determines the concentration of magnetic ballast in sludge blanket 200, similar as discussed above with reference to FIG. 4. The result is system 10', FIG. 7, effectively determines the location of sludge blanket 200 in clarifier 202. This allows sludge removal from clarifier 202 to be controlled by following the upper and/or lower accepted levels for sludge blanket 200 in clarifier 202. In another example, system 10, indicated at 240, may be submerged in clarifier 202 to determine the concentration of magnetic ballast in sludge blanket 200, similar as discussed above with reference to FIG. 1.

Figure 8:
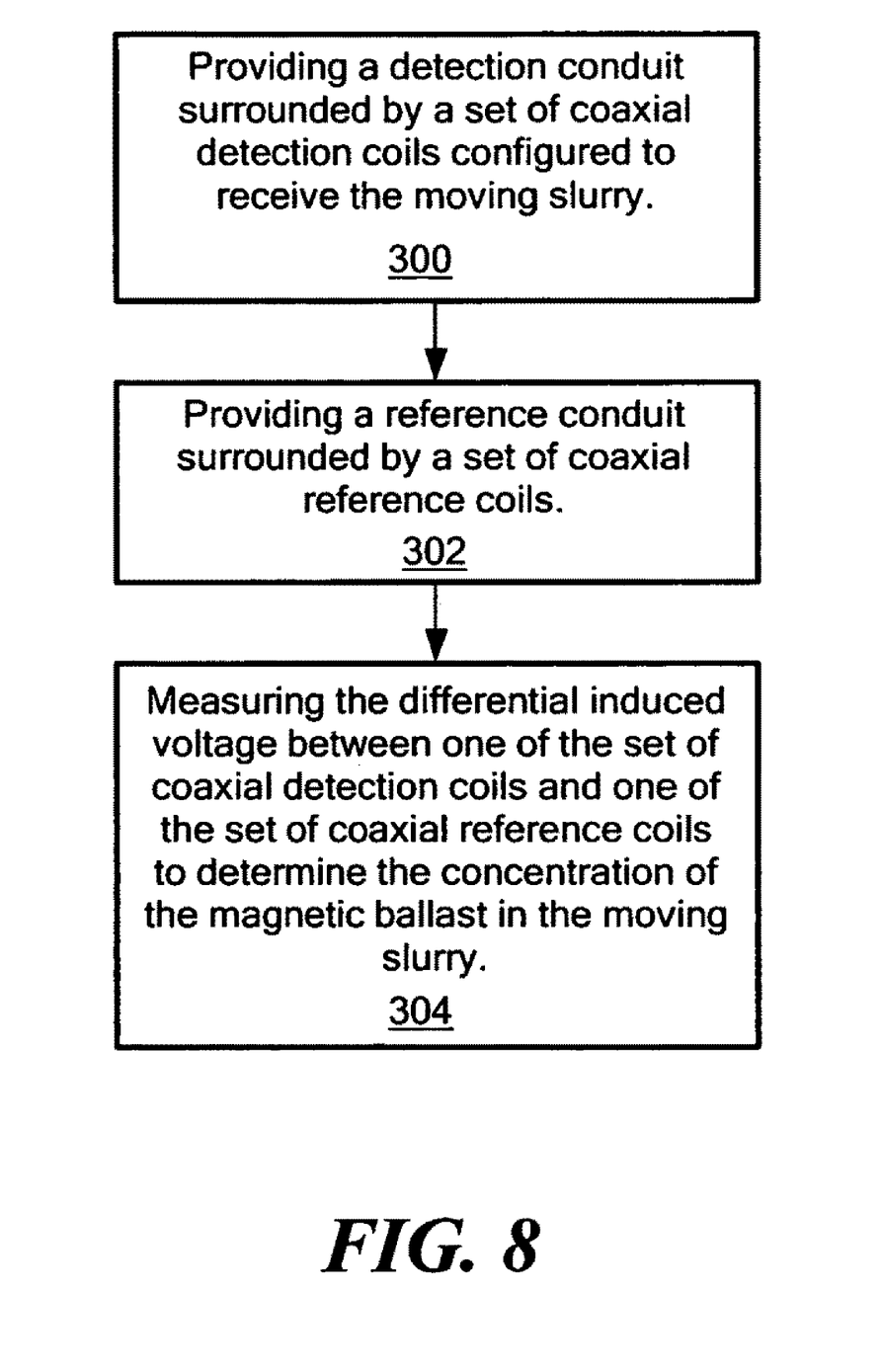
FIG. 8 is a schematic block diagram showing the primary steps associated with one embodiment of the method for measuring the concentration of magnetic ballast in a moving slurry.

The method for measuring the concentration of a magnetic ballast in moving slurry of this invention includes providing a detection conduit surrounded by a set of coaxial detection coils configured to receive the moving slurry, step 300, FIG. 8; providing a reference conduit surrounded by a set of coaxial reference coils, step 302, and measuring the differential induced voltage between one of the set of coaxial detection coils and one of the set of coaxial reference coils to determine the concentration of the magnetic ballast in the moving slurry, step 304, FIG. 6.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:

1. A system for measuring the concentration of magnetic ballast in a moving slurry comprising:
   a detection conduit surrounded by a set of coaxial detection coils configured to receive the moving slurry;
   a reference conduit surrounded by a set of coaxial reference coils;
   an AC power source for establishing a magnetic field in one of the detection coils and one of the reference coils; and
   a measurement subsystem for measuring the differential induced voltage between one of the set of coaxial detection coils and one of the set of coaxial reference coils to determine the concentration of the magnetic ballast in the moving slurry.

2. The system of claim 1 in which the measured voltage is proportional to the concentration of the magnetic ballast in the moving slurry.

3. The system of claim 1 in which one of the set of coaxial detection coils is connected in series with one of the set of coaxial reference coils and with the AC power source and the other of set of coaxial detection coils is connected back-to-back with the other of the set of coaxial reference coils and with the measurement subsystem.

4. The system of claim 1 further including a DC coil coupled to a DC power source surrounding one of the detection coils and the detection conduit for establishing a magnetic field which stops and collects magnetic ballast in the detection conduit so that the measurement subsystem can measure very low concentrations of magnetic ballast in the moving slurry.

5. The system of claim 4 in which the very low concentrations of magnetic ballast in the moving slurry is less than about 0.01 g/L.

6. The system of claim 1 further including a permanent magnet surrounding one of the detection coils and the detection conduit for establishing a magnetic field which stops and collects magnetic ballast in the detection conduit so that the measurement subsystem can measure very low concentrations of magnetic ballast in the moving slurry.

7. The system of claim 6 in which the very low concentrations of magnetic ballast in the moving slurry is less than about 0.01 g/L.

8. The system of claim 1 further including a pumping subsystem for directing the moving slurry to the detection conduit.

9. The system of claim 8 in which the pumping subsystem directs the moving slurry from a component of a wastewater treatment system to the detection conduit and back to the component of the wastewater treatment system.

10. The system of claim 1 in which one or both of the detection conduit and/or the reference conduit are immersed in the moving slurry of a component of a wastewater treatment system.

11. The system of claim 10 in which the component of a wastewater treatment system includes a component chosen from the group consisting of: a reaction tank, a mixing tank, an aeration tank, a settling tank, a clarifier, one or more lines and/or pipes, an impregnation subsystem, a return activated sludge subsystem, a weighting agent, recovery subsystem, and a wasting subsystem.

12. The system of claim 1 in which the detection coil is immersed in the moving slurry of a component of a wastewater treatment system and the reference conduit is disposed outside the component of the wastewater treatment system.

13. The system of claim 1 in which the moving slurry includes a mixed liquor defined by a concentration of mixed liquor suspended solids and biological flocs impregnated with magnetic ballast suspended in the mixed liquor.

14. The system of claim 1 in which the moving slurry includes chemical flocs and/or suspended solids having magnetic ballast therein and/or suspended magnetic ballast.

15. The system of claim 1 which the moving slurry includes a sludge blanket in a clarifier.

16. The system of claim 15 which the measurement system is configured to determine the location of the sludge blanket in the clarifier.

17. The system of claim 1 in which each of the set of coaxial reference coils and each of the set of coaxial detection are identical and symmetrical.

18. The system of claim 1 in which the magnetic ballast includes magnetically separable particles.

19. The system of claim 18 in which the magnetically separable particles include magnetite.

20. A method for measuring the concentration of magnetic ballast in a moving slurry, the method comprising:
    providing a detection conduit surrounded by a set of coaxial detection coils configured to receive the moving slurry;
    providing a reference conduit surrounded by a set of coaxial reference coils;
    establishing a magnetic field in one of the detection coils and one of the reference coils; and
    measuring the differential induced voltage between one of the set of coaxial detection coils and one of the set of coaxial reference coils to determine the concentration of the magnetic ballast in the moving slurry.

21. The method of claim 20 in which the measured voltage is proportional to the concentration of the magnetic ballast in the moving slurry.

22. The method of claim 20 further including the step of establishing a magnetic field which stops and collects magnetic ballast in the detection conduit so that the measurement subsystem can measure very low concentrations of magnetic ballast in the moving slurry.

23. The method of claim 20 in which the very low concentrations of magnetic ballast in the moving slurry is less than about 0.01 g/L.

24. The method of claim 20 further including the step of directing the moving slurry to the detection conduit.

25. The method of claim 20 further including the step of directing the moving slurry from a component of a wastewater treatment system to the detection conduit and back to the component of a wastewater treatment system.

26. The method of claim 20 further including the step of immersing one or both of the detection conduit and/or the reference conduit in the moving slurry of a component of a wastewater treatment system.

27. The method of claim 26 in which the component of a wastewater treatment system includes a component chosen from the group consisting of: a reaction tank, a mixing tank, an aeration tank, a settling tank, a clarifier, one or more lines and/or pipes, an impregnation subsystem, a return activated sludge subsystem, a weighting agent recovery subsystem, and a wasting subsystem.

28. The method of claim 20 further including the step of immersing the detection conduit in the moving slurry and disposing the reference conduit outside the component of the wastewater treatment system.

29. The method of claim 20 in which the moving slurry includes a mixed liquor defined by a concentration of mixed liquor suspended solids and biological flocs impregnated with magnetic ballast suspended in the mixed liquor.

30. The method of claim 20 in which the moving slurry includes chemical flocs and/or suspended solids having magnetic ballast therein and/or suspended magnetic ballast.

31. The method of claim 20 in which the moving slurry includes a sludge blanket in a clarifier.

32. The method of claim 31 further including the step of determining the location of the sludge blanket in the clarifier.

33. The method of claim 20 in which each of the set of coaxial reference coils and each of the set of coaxial detection coils are identical and symmetrical.

* * * * *